United States Patent
Chaudhuri

(10) Patent No.: US 10,828,241 B2
(45) Date of Patent: *Nov. 10, 2020

(54) SKIN LIGHTENING COMPOSITIONS AND METHODS

(71) Applicant: SYTHEON LIMITED, Boonton, NJ (US)

(72) Inventor: Ratan K. Chaudhuri, Lincoln Park, NJ (US)

(73) Assignee: SYTHEON LIMITED, Boonton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/427,274

(22) Filed: May 30, 2019

(65) Prior Publication Data

US 2019/0380935 A1    Dec. 19, 2019

Related U.S. Application Data

(60) Provisional application No. 62/685,406, filed on Jun. 15, 2018.

(51) Int. Cl.
  *A61K 8/35* (2006.01)
  *A61K 8/34* (2006.01)
  *A61Q 19/02* (2006.01)

(52) U.S. Cl.
  CPC .............. *A61K 8/35* (2013.01); *A61K 8/347* (2013.01); *A61Q 19/02* (2013.01)

(58) Field of Classification Search
  None
  See application file for complete search history.

(56) References Cited

U.S. PATENT DOCUMENTS

| | | | |
|---|---|---|---|
| 3,708,540 A * | 1/1973 | Yokotani | A61K 31/12 568/308 |
| 5,853,705 A | 12/1998 | Nakayama et. al. | |
| 8,414,870 B2 | 4/2013 | Chaudhuri | |
| 8,617,528 B2 | 12/2013 | Chaudhuri | |
| 8,765,101 B2 * | 7/2014 | Marion | A61K 8/35 424/59 |
| 2008/0305059 A1 | 12/2008 | Chaudhuri | |
| 2012/0141394 A1 | 6/2012 | Chaudhuri | |
| 2012/0141395 A1 | 6/2012 | Chaudhuri | |
| 2016/0256368 A1 * | 9/2016 | Santhanam | A61K 8/342 |

FOREIGN PATENT DOCUMENTS

| | | | |
|---|---|---|---|
| EP | 0797984 A2 | 1/1997 | |
| WO | WO-2012131072 A1 * | 10/2012 | A61Q 19/08 |

OTHER PUBLICATIONS

International Search Report and Written Opinion for PCT/US2019/34813, Int'l PCT equivalent to instant application, dated Aug. 23, 2019.

* cited by examiner

*Primary Examiner* — Sin J Lee

(74) *Attorney, Agent, or Firm* — IP&L Solutions; Edward K Welch, II

(57) ABSTRACT

Compositions and methods for effecting skin lightening and/or even toning involving the use of select aryl alkanones.

19 Claims, No Drawings

SKIN LIGHTENING COMPOSITIONS AND METHODS

RELATED APPLICATION

The present patent application claims the benefit of U.S. Provisional Application Ser. No. 62/685,406 filed Jun. 15, 2018, entitled "Skin Lightening Compositions and Methods," the contents of which are incorporated herein by reference in their entirety.

FIELD OF THE INVENTION

This invention relates to skin lightening/even toning compositions for lightening normal and/or hyper-pigmented skin comprising (i) one or more aryl alkanones, (ii) optionally, at least one other skin lightening agent, and (Ni) a dermatologically acceptable carrier. Additionally, the present invention relates to the use of these compositions and their method of use in effecting skin lightening/even toning of one's natural skin coloration or pigmentation as well as skin darkening, whether overall or in particular areas or as spots, resulting from sun exposure, other environmental and/or chemical (including medicinal) exposures, laser and other light based therapies, acne or other medical conditions that result in scar-induced hyperpigmentation, and skin aging, including age spots, liver spots, freckles, melasma, etc.

BACKGROUND OF THE INVENTION

Human skin color is quite variable around the world. It ranges from a very dark brown among some Africans, Australians and Asian-Indians to a near pinkish yellow among some northwest Europeans. There are no people who truly have black, white, red or yellow skin. These are commonly used terminologies that do not reflect biological reality. Skin coloration in humans arises from a complex series of cellular processes that are carried out within that population of cells known as the melanocytes located in the lower part of the epidermis. These processes result in the synthesis and transfer of a pigment, melanin, which, besides being responsible for skin color and tone, is the key physiological defense against sun-induced damage, such as sunburn, photoaging and photocarcinogenesis.

The mechanism by which melanin is produced is known as melanogenesis. The so formed melanin is accumulated/deposited in melanosomes, vesicles found within the melanocyte cells, which are subsequently transferred from the melanocytes and taken up and internalized by the keratinocytes, which then carry them to the surface of the skin. Generally speaking, skin coloration is primarily regulated by the amount and type of melanin synthesized by the epidermal melanocyte. However, additional and equally contributing factors include (a) the efficiency of the transfer of the melanosomes, hence the melanin, from the melanocytes to the neighboring keratinocytes and (b) the subsequent distribution and degradation of the transferred melanosomes by the recipient keratinocytes. Environmental factors can also markedly affect skin color. For example, exposure of the skin to ultraviolet light markedly influences and increases the amount and rate of melanin production, most often producing a further darkening of the skin or a "tan." Conversely, exposure to other factors, especially agents that interfere with melanin production and/or the transfer of melanin, may result in a decrease of melanin production and/or the rate or efficiency of its transfer resulting in a lightening of the skin.

Hyperpigmentation, hypopigmertation, and other pigmentation disorders are quite common and can arise from a number of causes including diet, medications and the like. Common pigmentation disorders include melasma (dark patches experienced in pregnancy), liver spots (which often develop with age), and may arise as a side effect of birth control pills, and/or as a persistent result of acne, burns, bites and other skin injuries, and vitiligo. Similarly, freckles, chloasma and pigmentary deposits after sun exposure tend to occur or increase or become difficult to disappear with increasing age, thus being one of the more disconcerting and/or common problems of skin care for persons of middle to advanced age. Post inflammatory hyper-pigmentation is also found to occur following laser therapy and in acne-affected skin.

In an effort to address such pigmentation disorders, various preparations have been formulated for use in the treatment of age spots and freckles or to obtain even-toning effects. Such treatments are not, however, limited for use in treating disorders but are also used in some cultures/markets merely for the purpose of changing or modifying natural skin color. Such treatments are typically referred to by a number of different terminologies including "skin lightener," "skin whitener," "skin even-toner," and "skin brightener." The specific terminology used is oftentimes a matter of regulatory controls; rather than one of performance or application. For example, "skin whitening" terminology is very commonly used in Asia whereas such terminology is not allowed under US Food and Drug Administration regulations. Other terminologies are commonly used as well including "melanin inhibitory agents." "depigmenting agents," "tyrosinase inhibitors" (tyrosinase being the key enzyme responsible for melanin synthesis), etc. Whatever terminology is employed, the general premise is that they all relate to a reduction in the formation or rate of formation of melanin. In this specification, the "depigmentation agent." "skin lightener," and "even-toner" terminologies will most often be used as they are physiologically more relevant.

A number of agents and methods for skin lightening have been developed and put on the market. Such methods include the oral administration of large doses of Vitamin C, the parenteral administration of glutathione, the topical administration of peroxide bleaching agents such as hydrogen peroxide, zinc peroxide, sodium peroxide and the like, and the topical application of Vitamin C and/or cysteine. Vitamin C, however, has stability issues, especially in water-based formulations, resulting in color and odor changes. Thiol compounds such as glutathione and cysteine have slow and/or generally poor depigmentation performance properties.

Perhaps the most commonly employed depigmentation agent has been hydroquinone and its derivatives; however, these compounds, while effective, have serious detrimental side effects. For example, even at concentrations below 2%, hydroquinone is both irritating and cytotoxic to the melanocytes. With the growing concern as to their safety, hydroquinone and its derivatives are largely being phased out of use or banned altogether in topical applications. Similar problems have been experienced with Kojic acid depigmentation agents as well.

A wide-range of polyphenols present in plant extracts have also been used for skin lightening/even-toning purposes. Melanin inhibitory activity of natural polyphenols, such as, anthraquinones (K Jones, J Hughes. M Hong. Q Jia, S Orndorff, Modulation of melanogenesis by aloeosin: a competitive inhibitor of tyrosinase. Pigment Cell Research, 15, 335-340, 2002), arylbenzofurans (S H Lee, S Y Choi, H Kim, J S Hwang, B G Lee, Mulberoside F isolated from the leaves from the leaves of *Murus alba* inhibits melanin biosynthesis, Bio Pham Bull, 25, 1045-1048, 2002), chalcones (O Nerya, R Musa. S Khatib, S Tamir, J Vaya, Chalcones as potent tyrosinase inhibitors: the effect of hydroxyl positions and numbers, Phytochem, 65, 1389-1395, 2004), coumarins (Y Masamoto. Y Murata, K Baba, Y Shimoishi, M Tada, K Takahata. Inhibitory effects of esculetin on melanin biosynthesis, Biol Pharm Bull, 27, 422-425, 2004), flavonoids (Y Yokoto, H Nishio, Y Kubota, M Mizoguchi. The inhibitory effect of glabridin from licorice extracts on melanogenesis and inflammation, Pigment Cell Research, 11, 355-361, 1998; J K No, D Y Soung, Y J Kim, K H Shim, Y S Jun, S H Rhee, R Yokozawa, H Y Chung, Inhibition of tyrosinase by green tea components, Pharmacol Letters, 65, 241-246, 1999; O Nerya, J Vaya, R Musa, S Izraef, R Ben-Arie, S Tamir, Glabrene and Isoliquiritigenin as tyrosinase inhibitors fro Licorice roots, J Agr Food Chem, 51, 1201-1207, 2003; I Kubo, I Kinst-Hori, S K Chaudhuri, Y Kubo, Y Sanchez, T Ogura, Flavonols from Heterotheca inuloides: Tyrosinase inhibitory activity and structural criteria, Bioorganic & Medicinal Chemistry, 9, 1749-1755, 2000), stilbenes (N H Shin, S Y Ryu, E J Choi, S H Kang, I M Chang, K R Min, R Kim, Oxyresveratrol as the potent inhibitor on dopa oxidase activity on mushroom tyrosinase, Biochem Biophys Res Commun, 243, 801-803, 1998; Y M Kim, J Yun, C K Lee. H Lee, K R Min, Y Kim, Oxyresveratrol and hydroxystilbene compounds, J Biol Chem, 277, 16340-16344, 2002); low molecular tannins (R K Chaudhuri, Z Lascu and G Puccetti, Inhibitory effects of *Phyllanthus emblica* tannins on melanin synthesis, Cosmetics & Toiletries, 122(2), 73-80, 2007) have been reported. Exemplary patents that describe the use of natural and synthetic phenolic compounds as skin tighteners include: U.S. Pat. No. 6,649,150—Chaudhuri et al.; U.S. Pat. No. 6,969,509—Chaudhuri et al.; U.S. Pat. No. 5,670,154—Hara et al.; and U.S. Pat. No. 5,880,314-Shinomiya et. al.

One class of polyphenolic compounds that has received a lot of attention as skin lightening agent, both commercially and in the patent literature, is that based on substituted resorcinols and their derivatives. Early applications, including U.S. Pat. No. 4,959,393—Torihara et. al., employed n-alkyl substituted resorcinol, especially those based on $C_2$ to $C_{12}$ n-alkyl substituted resorcinol. Subsequent applications, including JP 5-04905—Hamazaki et. al. and WO 2006/049184—Fukunishi et. al., focused on compositions containing 4-alkylresorcinol derivatives including straight chain and branched $C_2$ to $C_{12}$ 4-alkyl substituted resorcinols and their salts. Others still employed such 4-alkylresorcinols, especially 4-n-butylresorcinol, in combination with certain branched polymers, e.g., acrylic acid-alkyl methacrylate, wee e.g., JP 2001-010925—Seto et. al.

Though early activity seemed to focus on the simple alkyl substituted resorcinols, much greater focus has more recently been directed to more complex hydrocarbyl and/or hetero moiety substituted resorcinols. Hetero-substituted resorcinols include the thio, thiane (especially dithiane), amide, amine, keto and carboxylic substituted resorcinols as shown in U.S. Pat. No. 5,468,472-LaGrange et. al.; U.S. Pat. No. 6,875,425—Harichian et. al.; U.S. Pat. No. 6,852,310—Harichian et. al.; and JP 1125563—Sakai. Perhaps the greatest attention has focused on the more complex hydrocarbyl substituted resorcinols, specifically, the cycloalkyl resorcinols and substituted derivatives thereof. Such skin lightening agents are more fully described in, e.g., US 2006/0257340—Nair; U.S. Pat. No. 6,878,381—Colington; U.S. Pat. No. 6,933,319—Browning et al.; U.S. Pat. No. 6,852,747—Bradley et. al.; U.S. Pat. No. 6,828,460—Browning et. al.; U.S. Pat. No. 6,797,731—Bradley et. al.; U.S. Pat. No. 6,590,105—Bradley et. al.; U.S. Pat. No. 6,541,473—Bradley et. al.; and U.S. Pat. No. 6,132,740—Hu.

Despite the significant focus on substituted resorcinols and their derivatives, they too are not without their problems. For example, despite their relatively good skin lightening capabilities, they tend to suffer from stability issues, particularly color stability, rendering then generally unsuitable for topical applications. While the stability issues are most severe with the straight chain and branched alkyl substituted resorcinols, they are not limited thereto. Indeed, many, if not most, phenolic based skin lightening agents, whether synthetic or natural extracts, are susceptible to air and/or UV oxidation; thus, leading to color instability which also oftentimes coincides with loss of skin tightening efficacy. In following, efforts have been undertaken to improve their stability by the incorporation of various additives including metal oxides (U.S. Pat. No. 6,863,897—Love et. al.) and terpenoids (U.S. Pat. No. 6,858,217—Kerschner et. al.); however, their success has been limited.

Another significant detriment to the use of substituted resorcinols and their derivatives has been their relatively high level of byproducts and contaminants. Specifically, commercial grade resorcinols tend to be rather crude, containing significant levels of other polyphenols as well as resorcinol itself, owing to their relatively inefficient production processes and syntheses. For example, commercial grade $C_2$-$C_{12}$ alkyl-resorcinols are typically only on the order of 64-86% purity. The high level of impurities only adds to the stability concerns. More importantly, the presence of resorcinol and other undesired phenols and polyphenols also add concerns of skin irritancy and sensitization problems as well as other skin and health concerns. For example, resorcinol is a known skin irritant and sensitizer and has been associated with producing allergic dermatitis in a small proportion of individuals exposed repeatedly to resorcinol-containing cosmetic and pharmaceutical products. Resorcinol has also been found to be irritating to the eyes, the skin and the respiratory tract and is suspected of causing effects on the blood, resulting in formation of methaemoglobin. Although some of the more complex resorcinol derivatives mentioned above, especially the cycloalkyl substituted resorcinols, may have higher purity and, thus, avoid or lessen these concerns, they are oftentimes found to be less effective as skin lightening agents.

There remains a need for skin lightening agents and methods that do not suffer from instability, especially oxidative instability, that affects the color and efficacy of the skin lightening composition and the cosmetic/treatment formulation into which the skin lightening agents are incorporated.

There remains a need for skin lightening agents and methods that do not possess or raise concerns relative to skin irritancy and sensitization, or other possible skin or health consequences.

In general, there remains a need for additional skin lightening agents and methods, especially ones of high efficacies. Most especially, there remains a need for skin lightening agents and methods that are highly efficacious, stable and non-irritating.

Further, there is also a need for skin lightening agents that are compatible with and, most preferably, work synergistically with other skin lightening agents, especially in ways that enable the use of less skin lightening actives without compromising efficacy.

Finally, there remains a need for skin lightening compositions that achieve any or all of the foregoing objectives formulations and that are easy to use with highly efficacious results. In particular there remains a need for skin lightening compositions based on synergistic combinations of skin lightening agents or actives wherein the overall amount of the agents to be used are less than would be needed with either agent on their own.

SUMMARY

Surprisingly, it has now been found that certain aryl alkanones and their application, especially their topical application, to human skin provides a significant and marked effect in minimizing, most especially in reversing, skin pigmentation and in promoting skin lightening and even toning. Specifically, in accordance with the present teaching there are provided compositions for and methods of treating skin to mitigate, prevent and/or reverse the manifestation of skin pigmentation, especially hyperpigmentation, and/or provide a more even coloration or toning to the skin, said method comprising applying to the skin one or more skin lightening compositions comprising one or more aryl alkanones corresponding to the general Structure 1

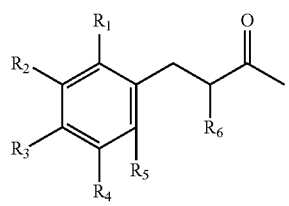

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and R6 is COCH3 or CO2R7, wherein R7 is a linear or branched alkyl having 1 to 8 carbon atoms, preferably from 1 to 6 carbon atoms, most preferably from 1 to 4 carbon atoms in a skin lightening effective amount.

Preferred groups of compounds according to Structure 1 include the following:

Group A: $R_1$, $R_2$, and $R_5$ are H; $R_4$ is an alkyl or alkoxy group of from 1 to 8, preferably from 1 to 6, more preferably from 1 to 4, carbon atoms, most preferably $OCH_3$; and $R_6$ is $COCH_3$ or $CO_2C_2H_5$;

Group B: $R_1$ and $R_5$ are H, $R_2$ and $R_4$ are $OCH_3$, $R_3$ is OH, and $R_6$ is $COCH_3$ or $CO_2C_2H_5$;

Group C: $R_1$, $R_2$ and $R_5$ are H, $R_4$ is $OCH_3$, $R_3$ is OH, and $R_6$ is $COCH_3$ or $CO_2C_2H_5$; and Group D: $R_1$, $R_2$ and $R_5$ are H, $R_4$ and $R_3$ are alkoxy groups of from 1 to 8, preferably from 1 to 6, more preferably from 1 to 4 carbon atoms, which may be the same or a different, and $R_6$ is $COCH_3$ or $CO_2C_2H_5$.

The most preferred aryl alkanone compounds for use in accordance with the present teaching are those compounds of Structure 2:

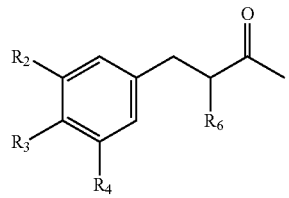

Structure 2 wherein $R_2$, $R_4$, $R_4$ and $R_6$ are as described above. Exemplary compounds include:

Compound 1 (Acetyl Zingerone): $R_2$ is H; $R_3$ is OH; $R_4$ is $OCH_3$; and $R_6$ is $COCH_3$;

Compound 2: $R_2$ is H; $R_3$ is OH; $R_4$ is $OCH_3$; and $R_6$ is $CO_2C_2H_5$;

Compound 3: $R_2$ and $R_4$ are H; $R_3$ is OH; and $R_6$ is $COCH_3$;

Compound 4: $R_2$ and $R_4$ are H; $R_3$ is OH; and $R_6$ is $CO_2C_2H_5$;

Compound 5: $R_2$ and $R_4$ are $OCH_3$; $R_3$ is OH; and $R_6$ is $COCH_3$;

Compound 6: $R_2$ and $R_4$ are $OCH_3$; $R_3$ is OH; and $R_6$ is $CO_2C_2H_5$;

Compound 7: $R_2$, $R_3$ and $R_4$ are $OCH_3$; and $R_6$ is $COCH_3$;

Compound 8: $R_2$, $R_3$ and $R_4$ are $OCH_3$; and $R_6$ is $CO_2C_2H_5$;

Compound 9: $R_2$ and $R_4$ are H; $R_3$ is $OCH_3$; and $R_6$ is $COCH_3$; and

Compound 10: $R_2$ and $R_4$ are H; $R_3$ is $OCH_3$; and $R_6$ is $CO_2C_2H_5$.

The skin lightening/even toning compositions envisioned by the present teachings comprise (i) one or more select aryl alkanones according to Structure 1, (ii) optionally, though preferably, at least one other skin lightening agent, and (iii) a dermatologically acceptable carrier. These compositions are especially effective for skin lightening/even toning and in controlling and/or reversing, in whole or in part hyperpigmentation, generally or localized on the skin.

While the aforementioned formulations are effective as skin lightening and even toning agents, they are also suitably employed as preventative compositions to be applied routinely, especially daily, for preventing the formation of sun-induced or laser therapy-induced skin darkening and/or or scar-induced or acne-induced hyper-pigmented spots as well as that resulting from other factors including diet and/or pharmaceutical agents.

The skin lightening/even toning compositions of the present invention will typically comprise one or more aryl alkanones in an amount of from about 0.01 to about 20 wt %, preferably from about 0.05 to about 10 wt %, more preferably from about 0.1 to about 5 wt %, most preferably from about 0.1 to about 2.5 wt % based on the total weight of the formulation. When used in combination with other conventional skin lightening agents, the second skin lightening agent will be present in an amount typical for that agent, generally on the order of from about 0.01 to about 20 wt %, preferably from about 0.05 to about 10 wt %, more preferably from about 0.1 to about 5 wt %, most preferably from about 0.1 to about 2.5 wt %, based on the total weight of the composition. Ideally, the combination of the alkanone and the second skin lightening agent provides a synergistic result wherein, though the aforementioned ranges still apply, the skin lightening/even toning effect of the combination of skin lightening agents is greater or more effective than for either skin lightening agent by itself at the same level of application, (n this respect, one can use less total skin lightening/even toning actives to achieve the same or better results than using the same amount of one skin lightening/even toning active, thereby also reducing the concerns or risks of sensitization, irritation, etc., while maintaining or achieving a high degree of skin lightening/even toning. Preferably, when both the aryl alkanone and the second skin lightening/even toning agent are used, the amount of each is in the range of from about 0.1 to about 5 wt %, more preferably from about 0.1 to about 2.5 wt %, based on the total weight of the composition.

In following, when the aryl alkanone (a) and the second skin lightening/even toning agent (b) are employed, the weight ratio of the two skin lightening agents will vary depending upon the selection of the second skin lightening agent; however, they will generally be present in a weight ratio of 20:1 to 1:20, preferably from 10:1 to 1:10, more preferably 5:1 to 1:5, most preferably 2:1 to 1:2, of (a):(b).

As noted, the skin lightening agent(s) are incorporated into dermatologically acceptable carriers to form topically applicable compositions. In addition to the skin lightening/even toning active(s), these skin lightening compositions may optionally include an effective amount of at least one additional skin protective and/or treatment ingredient such as sunscreens, antioxidants, vitamins, anti-inflammatory agents, moisturizers, emollients, humectants, and the like, and mixtures thereof, in their conventional amounts. Suitable carriers also include formulated base compositions used in the preparation of, for example, skin care health and beauty aid products, cosmetic compositions, pharmaceutical or therapeutic skin care products and the like, as well as such products themselves. The incorporation of the aryl alkanones is found to improve those products by adding their skin lightening/even toning effect to such products. This is especially desirable where the products themselves include ingredients that may cause or lead to hyperpigmentation.

The skin lightening compositions of the present invention are applied topically and may take the form of a cream, lotion, spray, ointment, gel, serum, or other any other topically applicable form. These compositions are applied generally to the skin or may be applied to specific areas of the skin for which skin lightening/even toning and/or prevention of hyperpigmentation is desired.

DETAILED DESCRIPTION OF THE INVENTION

As used in the present specification, the following terms shall have the meanings as presented:

A "dermatologically acceptable carrier" refers to a material that acts as a diluent, dispersant, vehicle or carrier for the stated actives, especially the aryl alkanone(s), and is recognized in the industry as acceptable or suitable for use, preferably long term use, in skin contact and, most preferably, without undue toxicity, incompatibility, irritability, allergic response and the like. Typically and to the extent appropriate or applicable, dermatologically acceptable carriers include those carriers that have been approved or are otherwise approvable by a regulatory agency of a government or governmental body or that are listed in the U.S. Pharmacopoeia or other generally recognized pharmacopoeia for use on humans. As used herein the term carrier also refers to base compositions used in formulating cosmetic, skin care, skin therapy and topical pharmaceutical products as well as such products themselves.

The terms "improves" and "improved" is used to convey, when referencing the skin and performance of the claimed compositions and methods, that there is a noticeable lightening and/or even toning of skin color in those areas of the skin to which the composition is applied and, when referencing cosmetic and other skin care products and compositions, that the application of the product or composition containing the aryl alkanone provides a noticeable lightening and/or even toning of skin color in the area(s) of the skin to which the product or composition has been applied.

A "noticeable lightening and/or even toning" of skin color means that the skin coloration of the areas to which the aryl alkanone was applied is more even and/or lighter than it was prior to application of the aryl alkanone and/or has darkened less than those areas where the aryl alkanone was not applied even though both areas were subjected to the same conditions and exposures. Efficacy is also evidenced by improved skin lightening and/or even toning as a result of the application of a composition containing the aryl alkanone as compared to the application of the same composition without the aryl alkanone. While a noticeable change may be detected by various sensors and like equipment, preferably the noticeable change is one that is detectable by human visual observation under sufficient light.

The term "effective amount" refers to the amount of the aryl alkanone and/or the composition containing the same that, when applied to the skin, is able to effect a noticeable skin lightening and/or even toning to the areas of the skin to which it is applied.

The term "topical" or "topically" refers to the application of the aryl alkanone and/or the composition containing the same onto the surface of the skin or a portion thereof.

The term "post-inflammatory hyperpigmentation" refers to the changes in melanin content as a response to an inflammatory event (e.g., acne, scratch, laser therapy, insect sting or bite, sunburn, etc.), especially in individuals of darker skin tone or color.

Erring on the side of caution and in an effort to avoid having overlooked or inadvertently omitted certain descriptive matter, particularly complementary and supplementary descriptive matter, it is hereby stated and affirmed that the technical publications as well as the patent and patent application publications mentioned herein are all incorporated herein in their entirety by this reference. Indeed, for example, while the current specification could present page after page of description of suitable dermatologically acceptable carriers, supplemental or ancillary ingredients, and co-actives as welt as various cosmetic and skin care compositions into which the aryl alkanones can be incorporated, such would not be productive as the same are well known and well recognized by those skilled in the art and those that come into being subsequent to the filing of this application will readily be appreciated as suitable as well.

In accordance with a first aspect of the present teaching there is provided a method of effecting skin lightening and/or even toning of skin color said method comprising applying to the skin or those areas of the skin for which skin lightening and/or even toning of skin coloration is desired one or more aryl alkanones corresponding to the general Structure 1

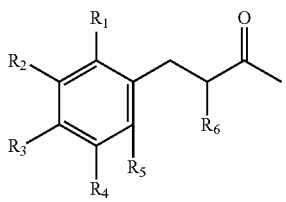

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms in a skin lightening effective amount. Preferably, the aryl alkanone is applied topically, optionally in combination with a second skin lightening agent, in a carrier or as a component of a skin care and/or cosmetic composition.

In accordance with a second aspect of the present teaching there is provided topical compositions for effecting lightening and/or even toning of skin color comprising an effective amount of one or more aryl alkanones corresponding to the general Structure 1

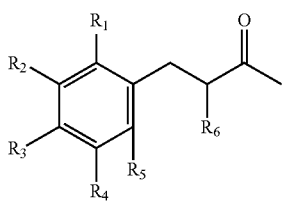

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in a dermatologically acceptable carrier. Optionally, such compositions may also comprise a second skin lightening agent. Such topical compositions typically comprise from 0.01 to 20, preferably, from 0.1 to 10 weight percent of the aryl alkanone based on the total weight of the composition.

In accordance with a third aspect of the present teaching there are provided improved cosmetic and skin care compositions, including therapeutic skin care compositions, wherein the improvement lies in the inclusion in such compositions of an effective amount, preferably from 0.01 to 20, more preferably from 0.1 to 10, weight percent, based on the total weight of the composition, of one or more aryl alkanones corresponding to the general Structure 1

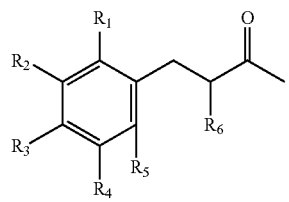

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms. Exemplary cosmetic and skin care compositions include make-up, foundation, rouge, moisturizing compositions, sunscreen compositions, lip balm, anti-aging and/or rejuvenating creams, and the like.

The key and critical aspect of the present teaching is the select aryl alkanones. As noted, aryl alkanones used in accordance with the present teaching correspond to Structure I

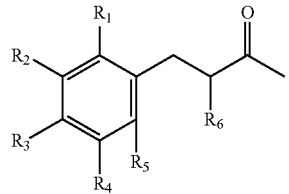

Structure 1 wherein $R_1$, $R_2$, $R_3$, $R_4$ and $R_5$ which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms.

Preferred groups of compounds according to Structure 1 include the following:

Group A: $R_1$, $R_2$, and $R_5$ are H; $R_4$ is an alkyl or alkoxy group of from 1 to 8, preferably from 1 to 6, more preferably from 1 to 4, carbon atoms, most preferably $OCH_3$; and $R_6$ is $COCH_3$ or $CO_2C_2H_5$;

Group B: $R_1$ and $R_5$ are H, $R_2$ and $R_4$ are $OCH_3$, $R_3$ is OH, and $R_6$ is $COCH_3$ or $CO_2C_2H_5$;

Group C: $R_1$, $R_2$ and $R_5$ are H, $R_4$ is $OCH_3$, $R_3$ is OH, and $R_6$ is $COCH_3$ or $CO_2C_2H_5$; and Group D: $R_1$, $R_2$ and $R_5$ are H, $R_4$ and $R_3$ are alkoxy groups of from 1 to 8, preferably from 1 to 6, more preferably from 1 to 4 carbon atoms, which may be the same or a different, and $R_6$ is $COCH_3$ or $CO_2C_2H_5$.

The most preferred compounds are those compounds of Structure 2 as follows:

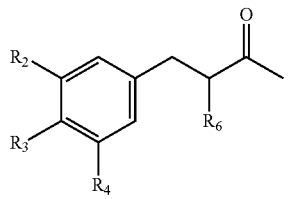

Structure 2

Exemplary preferred compounds include:
Compound 1 (Acetyl Zingerone): $R_2$ is H; $R_3$ is OH; $R_4$ is $OCH_3$; and $R_6$ is $COCH_3$;
Compound 2: $R_2$ is H; $R_3$ is OH; $R_4$ is $OCH_3$; and $R_6$ is $CO_2C_2H_5$;
Compound 3: $R_2$ and $R_4$ are H; $R_3$ is OH; and $R_6$ is $COCH_3$;
Compound 4: $R_2$ and $R_4$ are H; $R_3$ is OH; and $R_6$ is $CO_2C_2H_5$;
Compound 5: $R_2$ and $R_4$ are $OCH_3$; $R_3$ is OH; and $R_6$ is $COCH_3$;
Compound 6: $R_2$ and $R_4$ are $OCH_3$; $R_3$ is OH; and $R_6$ is $CO_2C_2H_5$;
Compound 7: $R_2$, $R_3$ and $R_4$ are $OCH_3$; and $R_6$ is $COCH_3$;
Compound 8: $R_2$, $R_3$ and $R_4$ are $OCH_3$; and $R_6$ is $CO_2C_2H_5$;
Compound 9: $R_2$ and $R_4$ are H; $R_3$ is $OCH_3$; and $R_6$ is $CO_2C_2H_5$; and
Compound 10: $R_2$ and $R_4$ are H; $R_3$ is $OCH_3$; and $R_6$ is $COCH_3$.

The aryl alkanone is applied or administered in an effective amount. Most typically, as noted above, the aryl alkanone is applied or administered as a component of a topical composition comprising the aryl alkanone in a dermatologically acceptable carrier, alone or together with one or mere co-constituents, which may be an active constituent which supplements the activity of the aryl alkanone and/or provides another benefit to the skin and/or as part of a topical pharmaceutical composition such as those used the treatment for psoriasis, atopic dermatitis, and the like, and/or as part of a common topical composition such as a sunscreen composition, cosmetic composition, moisturizer, etc.

Where the aryl alkanone is part of a composition, it is typically present in said composition in an amount which, when the composition is applied in accordance with the instructions or common practice, is sufficient to achieve a noticeable skin lightening and/or even toning effect. Typically, the amount of the aryl alkanone present in these compositions will be from about 0.01 to about 20 wt %, preferably from about 0.05 to about 10 wt %, more preferably from about 0.1 to about 5 wt %, most preferably from about 0.1 to about 2.5 wt %, based on the total weight of the composition. While the foregoing ranges are an excellent guide for formulating the claimed compositions, from a practical standpoint, it is also to be appreciated that the amount of the aryl alkanone used in the topical compositions and the amount of the so formed topical composition to be used is most desirably a safe amount: that is, an amount which is suitably efficacious, both from a performance and timing perspective, while low enough to minimize, if not avoid, any, especially any serious, side effects.

As noted above, optionally, though preferably, the skin lightening compositions of the present invention will also contain a second skin lightening/even-toning agent or ingredient. Many such suitable second skin lightening/even toning agents are mentioned in the patents and patent publications mentioned herein, especially in the background. Obviously, it is not be possible to list all known skin lightening agents, however, suitable examples include *Phyllanthus emblica* fruit extract, *Terminalia chebula* fruit extract, bearberry extract, mulberry extract, licorice extract, propolis extract, aceroal cherry fermentate, cucumber extract, Green tea poly phenols. Grape seed extract, Pine bark polyphenols, resveratrol, oxyresveratrol, stilbenes, coumarins, flavonoids, niacinamide, anthraquinones, xanthones, lignans, glabridin, curcurmine, dihydrocurcumine, tetrahydrocurcumine, epigallocatechin-3-gallate, hydroxyl benzoic acids or their derivatives, tomato glycolipids, perilla plant, ligusticum lucidum extract, bakuchiol, ascorbic acid and its derivatives including ascorbyl glucoside, ethyl ascorbic acid, and tetrahexyldecyl ascorbate, alkyl resorcinols, especially hexylresorcinol, butylresorcinol and phenylethyl resorcinol and combinations of any two or more of the foregoing. While certain polyphenol skin lightening agents such as the substituted resorcinols and their derivatives are especially desirable and beneficial, it is to be appreciated that may of the aforementioned resorcinols have considerable levels of impurities and other agents therein, particularly high or significant resorcinol contents. In following, it is preferred that the resorcinol skin lightening/even toning agents be of relatively high purity and/or have low resorcinol content. Otherwise, much of the benefit of the present invention may be compromised.

Other suitable skin lightening agents include the sugar amines, which are also known as amino sugars and are to be employed in a safe and effective amount. The sugar amine compounds useful in the present invention are described U.S. Pat. No. 6,159,485. Sugar amines can be synthetic or natural in origin and can be used as pure compounds or mixtures of compounds (e.g., extracts from natural sources or mixtures of synthetic materials). Glucosamine is generally found in many shellfish and can also be derived from fungal sources. As used herein, "sugar amine" includes isomers and tautomers of such and its salts (e.g., HCl salt) and is commercially available from Sigma Chemical Co. Examples of sugar amines that are useful herein include glucosamine, N-acetyl glucosamine, glucosamine sulfate, mannosamine, N-acetyl mannosamine, galactosamine, N-acetyl galactosamine, their isomers (e.g., stereoisomers), and their salts (e.g., HCl salt). Preferred ingredients are glucosamine, particularly D-glucosamine and N-acetyl glucosamine, particularly N-acetyl-D-glucosamine. Yet another group of skin lightening agents are the N-acyl amino acid compounds, including, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradename Sepiwhite™ from Seppic (France).

The combination of the aryl alkanones with the second skin lightening/even toning agents generally provides an additive effect and oftentimes provides a synergistic effect whereby the degree of skin lightening and/or even toning is improved as compared to either alone, even at the same total loading. This not only enables the use of less overall skin lightening agents for the same benefit but also reduces the concerns and potential for skin irritancy and sensitivity, especially with prolonged, repetitive use of a product. Furthermore, in addition to the additive and oftentimes synergistic effect seen with the combination of the aryl atkanone and the second skin lightening/even toning agents, it has also been found that the aryl alkanones significantly reduce, if not eliminate, the discoloration, especially the browning effect, oftentimes associated with many, if not most, skin lightening agents, especially those based on or containing phenolic groups/moieties, such as, *Phyllanthus emblica* fruit extract (Emblica® of EMD Chemicals), Licorice, resveratrol etc.

Like the aryl alkanone, the second skin lightening agent, if present, is present in an effective amount, generally an amount sufficient to induce the desired effect of skin lightening without or with minimal adverse side effects. The specific amount will vary depending upon the type of agent and the nature and level of desired effect. Typically the second skin lightening agents are present in an amount of from about 0.01 wt % to about 20 wt %, preferably from about 0.05 wt % to about 10 wt %, more preferably about 0.1 wt % to about 5 wt %, and most preferably about 0.1 wt % to about 2.5 wt %, based on the total weight of the composition. Generally speaking, given the additive and oftentimes synergistic effect with the combination of the aryl alkanones and the secondary skin lightening agents, the two are typically employed in the lower ranges mentioned above. Similarly, while the amount of either skin lightening agent will vary, so does the weight ratio of the two skin lightening agents: the variance depending upon the nature of the second skin lightening agent and the specific result desired. Generally, however, the weight ratio of the aryl alkanone to the second skin lightening agent or combination of agents will be from 20:1 to 1:20, preferably from 10:1 to 1:10, more preferably 5:1 to 1:5, most preferably 2:1 to 1:2.

In order to apply the aryl alkanones, most especially in order to topically apply the aryl alkanone to the skin, the aryl alkanones are combined with/incorporated into a dermatologically acceptable carrier or excipient, especially those carriers and excipients that are suitable for long term and repeated application to the skin without manifesting sensitization, irritation or inflammation. The specific carrier material will depend upon the delivery method itself. For example, as mentioned earlier, the skin lightening/even-toning compositions may be in the form of lotions, creams, gels, foams, emulsions, dispersions, sprays, liposomes, coacervates, etc. Each composition will typically include any of the known topical excipients and like agents necessary for achieving the particular form. Suitable excipients include, e.g., mineral oils, silicone oils and emulsifying agents. In its most simplest of embodiments, the carrier may be water, alcohol or water/alcohol combinations, or other solvent(s) or solvent systems in which the aforementioned actives may be, e.g., soluble, dispersed, emulsified, etc. Preferably, though, the skin lightening compositions will include excipients and the like that create a substantially stable, homogenous skin lightening/even-toning composition and/or provide body and viscosity to the skin lightening/even-toning composition so that the actives do not merely run off the skin once applied. Typically, the carrier will comprise from about 30 to about 99% by weight of the skin lightening composition.

Generally speaking, any known carrier or base composition employed in traditional cosmetic and/or dermatological applications/compositions may be used may be used in the practice of the present invention. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et al.—U.S. Pat. No. 7,101,536; Maniscalco—U.S. Pat. No. 7,078,022; Forestier et. al. U.S. Pat. Nos. 5,175,340, 5,567,418, 5,538,716, and 5,951,968; Deftandre et. al.—U.S. Pat. No. 5,670,140; Chaudhuri—U.S. Pat. Nos. 7,150,876, 6,831,191, 6,602,515, 7,166,273, 6,936,735, 6,831,191, and 6,699,463; Chaudhuri et. al.—U.S. Pat. Nos. 6,165,450 and 7,150,876; Bonda et. al., U.S. Pat. No. 6,962,692; Rodan et al.—U.S. Pat. No. 9,144,434, Wang et. al. U.S. Pat. No. 5,830,441 and Auspitz et. al.—US 2007/0110685 A.

The final form of these compositions and their method of manufacture depend, in part, upon the mode of administration as well as the other ingredients to be incorporated into the composition. Accordingly, the compositions containing the aryl alkanones may be in form of solutions, suspensions, emulsions, microcapsules, microcapsules containing liquids, powders, creams, lotions, gels, sustained-release formulations, emulsions, aerosols, sprays, suspensions, and the like. In following, the compositions may be prepared by means of conventional mixing, dissolving, granulating, dragee-making, levigating, emulsifying, suspending, encapsulating, etc. All of such options and methods are conventional in the art. Generally speaking, those skilled in the art will readily recognize and appreciate what carriers may be employed in light of the intended form and/or delivery method for the skin lightening/even-toning compositions.

As noted, the aryl alkanones are preferably incorporated into or combined with a carrier or other composition. Such compositions typically have as their primary objective the application of the aryl alkanone, however, it is also to be appreciated that the inclusion of the aryl alkanone in a topical composition is, in some instances, a supplemental or secondary objective. For example, the compositions optionally include an effective amount of one or more other skin protective and/or treatment ingredients such as antioxidants, sunscreen actives, vitamins, anti-inflammatory agents, moisturizers, emollients, humectants, other skin tighteners, anti-acne ingredients, compatible solutes and the like, and mixtures thereof, in their conventional amounts. Alternatively, or in addition thereto, these compositions also include other ingredients that have no or little bearing upon the intended end-use or application of the treatment aspect of these compositions, but aid in the preparation and/or longevity thereof, such as solubilizers, surfactants, stabilizers, thickeners, preservatives, buffers, etc. and/or the aesthetic qualities thereof, e.g., dyes, perfumes, scents, opactfiers, colorants, etc. Exemplary agents and additive materials are described briefly below as well as in the aforementioned patents, especially Maniscalco—U.S. Pat. No. 7,078,022. Furthermore, as previously mentioned the aryl alkanone can be incorporated into or added to existing skin care products, including cosmetics, general skin care products, rejuvenation products, topical pharmaceutical products, and the like, or into base compositions employed in the manufacture of the foregoing.

As those skilled in the art, it would be impossible to identify all of the possible active and non-active ingredients and additives that can be incorporated into the aryl alkanone compositions. Furthermore, any effort to endeavor to do so would run on for page after page. Nevertheless, in an effort to provide exemplary support, the following sections provide brief descriptions of some of the ingredients and additives contemplated.

Antioxidants are an especially desirable ingredient for skin care products. Suitable antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ethyl ascorbate, ascorbyl palmitate, tetra hexyldecyl ascorbate and ascorbyl polypeptide). Oil-soluble antioxidants suitable for use in the compositions of this invention include, but are not limited to, butylated hydroxytoluene, tocopherols (e.g., tocopherol acetate), tocotrienols, curcurmin and its derivatives and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, *Terminalia chebula* fruit extract, *Phyllanthus emblica* and propolis. A number of vitamins also have antioxidant properties and are more fully described below. Yet another group of suitable antioxidants include BHT (butylated hydroxy toluene), L-ergothioneine (available as Thiotane™); tetrahydrocurcumin, cetyl pyridinium chloride, carnosine, diethylhexyl syringylidene malonate (available as Oxynex® ST or Oxynex® ST Liquid available from EMD Chemicals/Merck, Germany.), ubiquinone (co-enzyme Q10), Idebenone and combinations thereof. Other examples of antioxidants may be found on pages 1612-13 of the ICI Handbook as well as in Ghosal—U.S. Pat. No. 6,124,268, both of which are incorporated herein by reference in their entirety.

Vitamins and/or their derivatives are another example of desirable active ingredients. Suitable vitamins and their derivatives include, but are not limited to, vitamin A, vitamin A propionate, vitamin A palmitate, vitamin A acetate, retinol, vitamin B, thiamine chloride hydrochloride (vitamin $B_1$), riboflavin (vitamin $B_2$), vitamin C and derivatives (for example ascorbyl palmitate, ascorbyl glucoside, and ascorbyl acetate, ethyl ascorbic acid, tetrahexydecyl ascorbate), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), niacinamide, pyridoxine, pyridoxal, pyridoxamine. (vitamin $B_6$), pantothenic acid, biotin, folic acid and cobalamine (vitamin $B_{12}$). Preferred vitamins are, for example, vitamin A palmitate, vitamin C and derivatives thereof, DL-α-tocopherol, tocopherol acetate, nicotinic acid, pantothenic acid and biotin. Vitamin E, which is often added to cosmetic and personal care products, is also preferably stabilized by a suitable stabilizer according to the invention.

Suitable emollients include those agents known for softening the skin which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxy stearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric triglycerides, propylene glycol dicaprylate/dicaprate and decyl oleate, cyclomethicones and other silicone derivatives. Suitable isosorbide diesters, a new class of hydrating emollients include, isosorbide dicaprylate (HydraSynol™ DOI, obtained from Sytheon) and Isosorbide disunflowerseedate (HydraSynol™ IDL, obtained from Sytheon).

Suitable humectants include various polyhydric alcohols, especially polyalkylene glycols and, more preferably, alkylene polyols and their derivatives. Exemplary humectants include propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin, compatible solutes, such as ectoin, hydroxyectoin, taurines, carnitine, acetyl carnitine and mixtures thereof. When employed in effective amounts, generally from 1 to 30%, preferably from 2 to 20%, by weight of the skin lightening/even toning composition, these additives serve as skin moisturizers as well as reduce scaling and stimulate the removal of built-up scale from the skin.

Compositions to be employed in preventing or addressing skin darkening arising from inflammation or inflammatory events, especially those employed to address post-inflammatory hyperpigmentation, preferably include one or more anti-inflammatory agents. Examples of anti-inflammatory ingredients include, but are not limited to, bisabolol, curcurmin and its derivatives, retinoids, flavonoids, bakuchiol, terpenes and other polyphenolics etc. These and other anti-inflammatory agents are disclosed in Gupta et. al.—US 2005/0048008A1, which is incorporated herein by reference in its entirety. Compositions containing steroidal anti-inflammatory, non-steroidal anti-inflammatory, as well as "natural" anti-inflammatory, such as extract of the plant Aloe vera, are also included in the present invention and have been disclosed for such use. Other anti-inflammatory ingredients are disclosed in, for example. Rovee—U.S. Pat. No. 4,185,100, issued Jan. 22, 1980 (hydrocortisone, dexamethasone, naproxen, ketoprofen, ibuprofen); Holick—U.S. Pat. No. 4,338,293, issued Jul. 6, 1982 (steroidal anti-inflammatories); Law, et al. Br. J. Pharmac., 59(4), 591-597 (1977) (ibuprofen); Kaidbey, J. Invest. Dermatoloy, 66, 153-156 (1976) (indomethacin); and Gruber, et al., Clinical Pharm. and Therapeut., 13(1), 109-113 (1971) (aspirin, fenoprofen).

Similarly, the aryl alkanone compositions may, and preferably do, contain active ingredients that have a plurality of benefits from the perspective of skin care and skin health. While many of these have already been identified above with respect to, perhaps, their most noted benefit, a preferred group of such ingredients or compounds are the retinoids, which, for the purpose of this disclosure include those natural and/or synthetic analogs of Vitamin A or retinol-like compounds which possess the biological activity of Vitamin A in the skin as well as the geometric isomers and stereoisomers of these compounds. Additionally, retinoids include those compounds that mimic retinol and retinoid compounds such as bakuchiol. The retinoid is preferably selected from retinol, retinol esters, retinoic acid esters e.g., $C_2$-$C_{22}$ alkyl esters of retinol or retinoic acid, including retinyl palmitate, retinyl acetate, retinyl propionate, hydroxypinacotone retinoiate, retinal, (including all-trans retinoic acid and/or 13-cis-retinoic acid), or mixtures thereof.

Inasmuch as it is nearly impossible to avoid sun exposure, and since sun exposure is associated with melanin product, it is desirable, especially where the aryl alkanone composition is to be applied to skin that is expose to the sun, to add one or more sunscreen actives to the aryl alkanone compositions. Sunscreen actives are of two types, inorganic actives that work by reflecting the UV light and organic actives that work, predominately, by absorbing UV energy. The amount of the sunscreen active to be incorporated into the sunscreen formulations is that which is conventional in the art. Typically, the amount is dependent upon, among other factors, the delivery means, e.g., is it applied as a spray or lotion; the stability of the active; the efficacy of the selected sunblock active itself; and the application rate, as well as the particular SPF desired. From the commercial perspective, another factor influencing the level of such sunscreen actives in the sunscreen formulations is the regulatory limitations on their use. In the United States, for example, strict controls are placed upon the maximum level at which approved sunscreen actives may be present. Regulatory controls may also dictate which sunscreen actives may be used in which countries.

Suitable organic sunscreen actives include, for example, butyl methoxydibenzoylmethane (avobenzone), benzophenone-8, dioxybenzone, homosalate, octylsalate, menthyl anthranilate, octocrylene, ethyhexyl methoxycinnamate (Octinoxate), oxybenzone, ethylhexyl salicylate (Octisalate), benzophenone-3, ethylhexyl dimethyl PABA (Padimate O), glyceryl PABA, phenylbenzimidazole sulfonic acid, sulfisobezone, trolamine salicylate, 4-methylbenzylidene camphor, bisoctriazole, bemothzinol, ecamsule, drometrizole trisiloxane, disodium phenyl dibenzimidazole tetrasulfonate, diethylamine hydroxybenzoyl hexyl bezoate, octyl triazone, hexyl benzoate, benzophenone-4, ethyhexyl triazone, diethylhexyl butamido triazone, bisimidazylate, polysilicone-15, etc.

Inorganic sunscreens include, but are not limited to, microfine surface treated titanium dioxide and microfine untreated and surface treated zinc oxide. The titanium dioxide in the sunscreen compositions preferably has a mean primary particle size of between 5 and 150 nm, preferably between 10 and 100 nm. Titanium oxide may have an anatase, rutile, or amorphous structure. The zinc oxide in the sunscreen compositions preferably has a mean primary particle size of between 5 nm and 150 nm, preferably between 10 nm and 100 nm.

Examples of suitable hydrophobically modified titanium dioxide compositions include but are not limited to: UV Titans® X161, M160, M262 (surface treated with stearic acid and alumina) (Kemira); Eusolex® T-2000 (surface treated with alumina and simethicone) (Merck KGaA); T-Cote® (surface treated with dimethicone) (BASF); Mirasun® TiW60 (surface treated with silica and alumina) (Rhodia); Tayaca MT100T (surface treated with aluminum stearate) (Tayaca); Tayaca MT-100SA (surface treated with silica and alumina) (Tayaca); Tayaca MT-500SA (surface treated with silica and alumina) (Tayaca); Tioveil® EUT, FIN, FLO, FPT, GCM, GPT, IPM, MOTG, OP, TG, TGOP (surface treated with silica and alumina, 40% dispersion in a range of cosmetic vehicles) (ICI); Eusolex® T-45D (surface treated with alumina and simethicone, 45% dispersion in isononoylnonaoate) (Merck KGaA); and Eusolex® T-Aqua (surface treated with aluminum hydroxide, 25% dispersion in water) (Merck KGaA).

Examples of suitable untreated and hydrophobically modified zinc oxide include but are not limited to; Z-Cote® (uncoated microfine zinc oxide) (BASF); Z-Cote® HP-1 (surface treated with dimethicone) (BASF); Sachtotec® LA 10 (surface treated with lauric acid) (Sachtleben); Sachtotec® (uncoated microfine zinc oxide) (Sachtleben); Spectraveil® FIN, IPM, MOTG, OP. TG, TGOP (uncoated, 60% dispersion in a range of cosmetic vehicles) (ICI); Z-sperse® TN (untreated, dispersion in C12-15 alkyl benzoate) (Collaborative); Z-sperse® TN (untreated, dispersion in octydodecyl neopentanoate) (Collaborative).

Most preferably, the skin lightening/even toning compositions of the present invention will comprise a combination of such sunscreen actives. In this respect, it is well known that certain sunscreen actives have better stability, hence longevity, than others; while others have better absorptive capabilities, whether in reference to selectivity for certain UV energy of certain wavelength(s) or cumulative absorptive capabilities. If needed, suitable photostabilizer, for examples, diethylhexyl bezylidene malonates (Oxynex® ST or Oxynex® ST Liquid marketed by EMD/Merck, Germany), 4-methylbenzylidene camphor, butyloctyl salicylate, diethylhexyl 2,6-naphthalate (Corapan® TQ, marketed by Symrise). Trimethoxybenzylidene Pentanedione (Synoxyl® HSS, marketed by Sytheon), Solastay® S1 (marketed by HallStar) etc. can also be included to stabilize unstable sunscreen actives. Additionally, synergistic agents may be used in combination with one or more sunscreen compositions including for example bakuchiol. Such synergistic combinations are disclosed in, the U.S. Pat. No. 8,529,967 titled "Sunscreen Compositions and Methods", which is incorporated herein by reference in its entirety. Hence, by using combinations of such UV sunscreen actives, one is able to provide greater prevention of sun-induced hyperpigmentation. Suitable combinations of sunscreen actives are well known in the art and within the skill of a typical artisan in the field.

The skin lightening/even-toning compositions of the present invention may also include one or more skin penetrants. These are additives that, when applied to the skin, have a direct effect on the permeability of the skin barrier: increasing the speed with which and/or the amount by which certain other compounds are able to penetrate into the skin layers. Exemplary organic penetration enhancers include dimethyl sulfoxide; isopropyl myristate; decyl, undecyl or dodecyl alcohol; propylene glycol; polyethylene glycol; $C_{9-11}$, $C_{12-13}$ or $C_{12-15}$ fatty alcohols; azone; alkyl pyrrolidones; diethoxy glycol (Transcutol); lecithin; etc. Surfactants can also be used as penetration enhancers.

Other optional adjunct ingredients for the skin lightening/even toning compositions of the present invention include preservatives, waterproofing agents, fragrances, anti-foam agents, plant extracts (Aloe vera, witch hazel, cucumber, etc), opacifiers, stabilizers, skin conditioning agents colorants, and the like, each in amounts effective to accomplish their respective functions.

As discussed above, the skin lightening/even toning compositions of the present invention may be prepared by any method known in the art for cosmetic and/or dermatological preparations. Generally, the method comprises the simple mixing of the components; though, especially where insoluble or immiscible components are employed, higher agitation or homogenization may be necessary to prepare an appropriate composition, e.g., an emulsion or suspension, etc. Additionally, during the preparation, it may be desirable to add known pH adjusters in order to maintain a proper pH of the composition for topical application, especially if basic ingredients are to be employed. Generally, the pH should be on the neutral to slightly acidic side, perhaps as low as pH 4. Preferably, though, the pH will be in the range of from about 5 to about 7, preferably from about 5 to 6.5.

The skin lightening/even toning compositions of the present invention are applied as either a preventative measure to prevent or inhibit skin darkening or as a treatment to address pre-existing skin darkening and/or uneven toning. In the former, the skin lightening/even toning compositions are applied to areas of the skin that are prone to skin darkening such as those exposed to sunlight, in the case of sun-induced hyperpigmentation, including melisma; that are prone to acne and other types of inflammation or skin damage or that are anticipated to undergo a treatment that is associated with inflammation, e.g., laser therapy, where post-inflammatory hyperpigmentation is likely to arise; as well as to areas of the skin where hyperpigmentation has already been reduced and it is desired to maintain a certain skin color and/or tone. In the latter, the skin lightening/even toning composition is applied to skin for which the individual desires a lighter color and/or a more even tone, especially skin which has developed hyperpigmentation and/or a blotchy or uneven coloration. For example, at one extreme one may desire to lighten the whole of their skin or just those areas that, due to long term sun and UV exposure are darker than the rest of the body. Indeed, vanity may prompt some individuals to use skin lightening and even toning to reduce the appearance of tan lines. More importantly, though, the present method, is directed to the lightening and even toning of spots and/or select areas of the skin where hyperpigmentation and/or uneven or blotch skin coloration has developed, most often as a result of physical and/or physiological events including trauma, inflammation, laser therapy, age, sun exposure, diet, drug or pharmaceutical treatment, pregnancy, etc. Most preferably, and beneficially, particularly from a psychological perspective, the present method is especially directed to the treatment of hyperpigmentation and uneven or blotchy skin coloration arising from trauma, inflammation, laser therapy, diet, drug or pharmaceutical treatment, pregnancy, and other biological conditions or diseases and/or their treatment, other than exposure to sun light and/or typical skin aging, in order to enable those stricken with the hyperpigmentation and/or uneven or blotchy skin coloration avoid the stigma and self-consciousness associated with those conditions. In this respect, age spots and sunspots arising from long-term sun exposure are the norm for aging adults; however, for children, teens and young adults who suffer/suffered from acne, eczema, vitiligo, melisma, etc., the appearance of such hyperpigmentation and/or uneven or blotchy toning is much more traumatic and, even if the unevenness as in vitiligo cannot be eliminated in total, it can be muted, any change is seen, particularly from a personal or psychological perspective, as a positive change.

The duration and frequency of application varies, as noted above. Generally speaking, the composition is applied until the desired skin lightening and/or even toning effect is attained. Where the composition is applied as a preventative measure, it will be applied for the duration of the circumstances giving rise to the potential for the hyperpigmentation, especially where post-inflammatory hyperpigmentation is of concern. Similarly, once the desired level of skin lightening and/or even toning it achieved, it may be desirable to apply a lesser amount of the aryl alkanone and/or apply it less frequently, in order to maintain the given skin color and tone.

The amount of the skin lightening/even toning composition that is to be applied to the skin depends upon the form of the skin lightening/even toning composition and its mode of application. Generally speaking, the amount is that which is sufficient to provide a thin film of the composition to the treated skin. Typically, a small quantity of the composition, for example from 0.1 to 5 ml, is applied to the skin from a suitable container or applicator and spread over and/or rubbed into the skin using the hands or fingers or a suitable device. Preferably, the aryl alkanone composition is applied at least once daily, more preferably at least twice daily, to the skin generally or to those areas of the skin for which skin lightening and/or even toning is sought until an the desired improvement in skin appearance is attained or becomes apparent. This time frame will vary markedly depending upon the extent of lightening and/or toning desired, the darkness of the skin and/or uneven toning of the skin to begin with, the frequency of application, the activity level of the individual and whether the composition is washed or worn away during such activities, as well as the concentration of the aryl alkanone in the composition and the presence of other ingredients which may boost or inhibit or delay the skin tightening effect of the aryl alkanone. Typical application periods will extend from 7 days to 6 months or more. Given the other benefits of the aryl alkanones, it may be desirable to continue the application of these compositions as a daily ritual, even after the desired skin lightening and/or even toning effect is achieved, improve overall skin health and/or to counter the effects of natural skin aging and, more importantly, the detrimental effects of sun exposure and air pollutants, tn this regard, a user may adopt a routine of application of a aryl alkanone composition where the aryl alkanone is the key or a key active ingredient to effect the desired skin lightening and/or even toning until the desired effect is attained followed by the use of a daily moisturizer, sunscreen and/or cosmetic composition that also contains the aryl alkanone as a constant preventative and therapeutic treatment.

For those compositions containing sunscreens and, in following, those methods for preventing hyperpigmentation from UV exposure, the skin lightening/even toning composition should be applied before sun exposure, preferably at least 15 minutes before, and reapplied at least every 2 hours or more frequently, especially if the individual engages in activities/actions that may cause the sunscreen containing skin lightening composition to wear or wipe off, e.g., swimming; washing dishes, windows, etc.; washing hands and/or face; contact sports activities; activities that promote substantial sweating; etc.: all actions/events that cause the premature wearing off or loss of the sunscreen containing composition.

EXAMPLES

Having described the invention in general terms, the following sets of examples will now demonstrate various embodiments of the inventive compositions and their use. In the following examples, unless otherwise indicated, all temperatures are set forth in degrees Celsius and all parts and percentages are by weight based on the total composition as applied to the skin.

Example 1: Clinical Study

To demonstrate the efficacy of the aryl alkanone a clinical study was undertaken in which acetyl zingerone sold by Sytheon Ltd., of Boonton, N.J. under the tradename Synoxyl® AZ was investigated. The test formulation (Formulation 1A) and a control formulation (Formulation 1B) containing the same ingredients but for the aryl alkanone were as presented in Table 1.

TABLE 1

| INCI name | Trade Name/Supplier | Formulation 1A | Formulation 1 B |
|---|---|---|---|
| Phase A-1 | | | Control |
| Water (demineralized) | | 79.7 | 80.7 |
| Glycerin | Glycerin 99%/Ruger | 3.00 | 3.00 |
| Phase A-2 | | | |
| Sodium acrylates copolymer, Lecithin | Lecigel/Lucas Meyer | 0.80 | 0.80 |
| Phase B | | | |
| Caprylic/Capric Triglycerides | Myritol 318/BASF | 4.00 | 4.00 |
| Steareth-10 | Brij S 10/Croda | 1.00 | 1.00 |
| Ceeareth-20, Cetearyl Alcohol | Ritapro 200/Rita | 2.50 | 2.50 |
| *Butyrospermum Parkii* (Shea) Butter | Shea Butter Refined/Rita | 1.00 | 1.00 |
| Cetyl Alcohol | Crodacol C-70/Croda | 1.00 | 1.00 |
| Isostearyl Lactate | Ritalac IL/Rita | 1.50 | 1.50 |
| Dimethicone | DC, 200/50 CST/Dow Corning | 0.50 | 0.50 |
| Phase C | | | |
| Isosorbide Dicaprylate | HydraSynol ® DOI/Sytheon | 4.00 | 4.00 |
| Acetyl Zingerone | Synoxyl ® AZ/Sytheon | 1.00 | — |
| Phase D | | | |
| Ethylhexylglycerine, Caprylyl Glycol | Lexgard OE/Innolex | 1.00 | 1.00 |
| Total | | 100.00 | 100.00 |

The test formulations were prepared by first combining the ingredients of Phase A-1 and then dispersing Phase A-2 in A-1 while stirring and heating to 75° C. Separately, the ingredients of Phase B are combined and heat to 75° C. Phase B was then added to the combined Phase A with good mixing. The mixture was then homogenized at high speed for 5 min and then cooled to 50° C. while slowly adding the premixed Phase C. The composition was then stirred gently until homogeneous and then cooled to 40° C. at which point Phase D was added while mixing, again until homogeneous. The resultant lotions had a pH of about 5.5 with a viscosity of 30,000-45,000 cps (Brookfield RVT, spindle C. Hetipath) at 25° C.

A total of 34 healthy individuals aged 35 to 55 years old who (1) had not applied topical antibiotics within the past 4 weeks; (2) had not taken oral antibiotics within past 4 weeks; (3) had not used systemic isotretinoin in the last 6 months; (4) did not report an allergy to members of the ginger family; (5) were not current smokers and neither had a 20 pack-year history of smoking nor had smoked within the past 3 years; (6) were not pregnant; (7) did not have any visible signs in the area of application of or on active treatment for cystic acne, eczema, seborrheic dermatitis, papulopustular rosacea at investigator discretion; and (8) had not had a recent surgical or cosmetic procedure in the last 3 months that can affect facial wrinkles or facial hyperpigmentation, such as botulinum toxin injections, chemical peels, laser based therapies to the face, or face lift surgeries participated in the study. Prior to beginning the study, each individual was instructed to wash their faces with Dove® soap only for approximately one week prior to the initial application of the test materials and throughout the duration of the study. Each individual was instructed not to wash their faces or body or apply any products to their face on the day of their first test visit. If the subjects had been using or had used topical ginger, topical turmeric, topical curcumin, beta hydroxyl acid, salicylic acid, and/or topical retinoids they were instructed to perform a washout of those substances tar one week prior to starting the one week washout with Dove® soap.

Digital visible light photography (no UV exposure) of the face and neck was taken of ail participants both on the first visit (to establish a baseline) and on each subsequent visit. The participants were then randomly divided into two groups of 17, with one group being treated with the lotion containing the acetyl zingerone and the other with the control: the lotions being generously applied to the full face of each individual. The lotions were applied twice daily for the duration of the trial; 10 weeks. Throughout the study, participants were evaluated by staff to note changes in the appearance of skin pigmentation as well as changes in skin redness (erythema) or the manifestation of any other side effects including scaling and irritation, including stinging, itching, and burning. This was in addition to the digital photographs taken on each visit. Once the test period was concluded a board-certified dermatologist, blinded to study group assignment, reviewed all the photographs and performed an assessment with respect to facial erythema, scaling, hyperpigmentation, and hypopigmentation.

Based on the staff observations as well as the assessment made by the dermatologist, it was determined that both test lotions. Formulations 1 and 2 were well tolerated and no adverse cutaneous side effects were observed. Tables 2 and 3 present the results for pigment intensity (Table 2) and skin redness (Table 3) at four and eight weeks for both formulations. As evident from the tables, the aryl alkanone provided a marked and significant reduction in pigment intensity, manifesting a strong skin lightening effect.

TABLE 2

| Study Duration | 4 weeks | 4 weeks | 8 weeks | 8 weeks |
|---|---|---|---|---|
| Pigment Intensity (% Change) | Compd. 1 | Control | Compd. 1 | Control |
| Average | −25.580 | −7.119 | −25.601 | −8.478 |
| Sid Error | 6.276 | 3.762 | 6.275 | 6.551 |
| Paired T-test | 0.006 | | 0.010 | |
| Adjusted p-value | 0.013 | | 0.021 | |

TABLE 3

| Study Duration | 4 weeks | 4 weeks | 8 weeks | 8 weeks |
|---|---|---|---|---|
| Degree of Redness Intensity (% Change) | Compd. 1 | Control | Compd. 1 | Control |
| Average | −17.902 | 14.677 | −20.682 | 19.692 |
| Std Error | 9.540 | 15.736 | 9.851 | 16.023 |
| Paired T-test | 0.040 | | 0.0175 | |
| Adjusted p-value | 0.080 | | 0.0351 | |

Example 2

A skin lightening formulation with sunscreens (Broad-spectrum SPF 30+) is prepared with the formulation as presented in Table 4. This composition is prepared by combining all the Phase A ingredients and then heating the mixture to 80-85° C. with stirring until free of solids. Separately, the Phase B ingredients are combined and mixed while heating to 70° C. with mixing continuing until the solids are fully solubilized. Thereafter, Phase B to is blended with Phase A and mixed until uniform. Once a homogeneous composition is attained the composition is poured into containers at 70° C.

TABLE 4

| INCI Name | Trade Name/Supplier | % w/w |
|---|---|---|
| Phase A | | |
| Octyldodecanol | Eutanol G/BASF | 29.30 |
| Diisobutyl Adipate | Dermol DIBA/Alzo | 10.00 |
| Dicaprylyl Ether | Cetiol OE/BASF | 15.00 |
| Isoamyl Laurate | Dermofeel Sensolv/Dr. Straetmans | 10.00 |
| Isosorbide Dicaprylate | HydraSynol ™ DOI/Sytheon | 4.00 |
| Phenethyl Benzoate | X-Tend 226/Ashland | 10.00 |
| Tocopheryl Acetate | Vitamin E Acetate/BASF | 0.20 |
| Acetyl Zingerone or a mixture of Acetyl Zingerone and Hexylresorcinol (1:1) | Synoxyl ® AZ/Sytheon Synovea ® HR/Sytheon | 1.00 |
| Phase B | | |
| Avobenzone | Eusolex 9020/EMD Chemicals | 3.00 |
| Trimethoxybenzylidene Pentanedione | Synoxyl ® HSS/Sytheon | 2.50 |
| Homosalate | Eusolex HMS/EMD Chemicals | 10.00 |
| Octyl Salicylate | Eusolex OS/EMD Chemicals | 5.00 |
| Total | | 100.00 |

Example 3

A skin even-toning spray with sunscreen (Broad-spectrum SPF 50+)(in-vivo SPF 56 (FDA protocol-5 subjects); CW-376) is prepared with the formulation as presented in Table 5. This composition is prepared by separately combining the ingredients for each of Phases A, B and C: the Phase B ingredients being combined and heated, while mixing, to 70° C. until it is completely free of solids. In the case of Phase C, the acetyl zingerone is solubilized in the other ingredients with slight heating. Thereafter. Phases A and C are added to Phase B at 50° C. with continued mixing.

TABLE 5

| INCI name | Trade Name/Supplier | % w/w |
|---|---|---|
| Phase A | | |
| Alcohol Denatured | SD Alcohol 40 B 200 | 40.00 |
| VA/Butyl Maleate/Isobornyl Acrylate Copolymer | Advantage Plus/Ashland | 2.00 |
| Phase B | | |
| Avobenzone | Eusolex 9020/EMD | 3.00 |
| Trimethoxybenzylidene Pentanedione | Synoxyl ®HSS/Sytheon | 2.50 |
| Homosalate | Eusolex HMS/EMD | 10.00 |
| Octyl Salicylate | Eusolex OS/EMD | 5.00 |
| Diisopropyl Adipate | Dermol DIA/Alzo | 10.00 |
| Phase C | | |
| Phenethyl Benzoate | X-tend 226/Ashland | 20.00 |
| C12-15 Alkyl Benzoate | Finsolv TN/Innospec | 5.00 |
| Acetyl Zingerone | Synoxyl ®AZ/Sytheon | 0.50 |
| Isosorbide Dicaprylate | HydraSynol ™ DOI/Sytheon | 2.00 |
| Total | | 100.00 |

Example 4

A skin even toning oil gel with sunscreens (Broad-spectrum—SPF 30+) is prepared with the formulation as presented in Table 6. This composition is prepared by combining all the Phase A ingredients and heat the combination to 80-85° C. with stirring until free of solids. Separately, the Phase B ingredients are combined at 70° C. and mixed until all the solids are fully solubilized. Thereafter, Phase B is blended into Phase A and mixed until uniform while maintaining the temperature at 70° C. Once a homogenous mixture is attained, the mixture is poured into containers at 70° C.

TABLE 6

| INCI Name | Trade Name/Supplier | % w/w |
|---|---|---|
| Phase A | | |
| Octyldodecanol | Eutanol G/BASF | 26.30 |
| Diisobutyl Adipate | Dermol DIBA/Alzo | 10.00 |
| Dicaprylyl Ether | Cetiol OE/BASF | 10.00 |
| Isoamyl Laurate | Dermofeel Sensolv/Dr. Straetmans | 10.00 |
| Isosorbide Dicaprylate | HydraSynol ™ DOI/Sytheon | 3.00 |
| Dextrin Palmitate | Rheopearl KI2/Miyoshi America | 5.00 |
| Phenethyl Benzoate | X-Tend 226/Ashland | 12.00 |
| Acetyl Zingerone | Synoxyl ® AZ/Sytheon | 0.50 |
| Dipropylene Glycol Dibenzoate, Dipropylene Glycol | Dermoblend SYN/Alzo | 2.50 |
| Tocopheryl Acetate | Vitamin E Acetate/BASF | 0.20 |
| Phase B | | |
| Avobenzone | Eusolex 9020/EMD Chemicals | 3.00 |
| Trimethoxybenzylidene Pentanedione | Synoxyl ® HSS/Sytheon | 2.50 |
| Homosalate | Eusolex HMS/EMD Chemicals | 10.00 |
| Octyl Salicylate | Eusolex OS/EMD Chemicals | 5.00 |
| Total | | 100.00 |

Example 5

A whipped skin lightening moisturizer is prepared with the formulation as presented in Table 7. This composition is prepared by combining the ingredients of Phase A-1 and dispersing Phase A-2 in Phase A-1 while stirring and heating the mixture to 75° C. The ingredients to Phase B are then combined and the mixture heated to 75° C. Thereafter, Phase B is added to the combined Phase A with good mixing and the combination homogenized at high speed for 5 min. Concurrently individually prepare Phase C and Phase D, neutralizing, as necessary the latter. Thereafter, cool the homogenous mixture of Phases A and B to 50° C. and slowly add Phase C. Once complete, add the pre-neutralized Phase D with high mixing. Cool the mixture to 40° C. and then add Phase E with mixing until uniform. The resulting composition has a pH of ~5.5 and a viscosity of 20,000-30,000 cps (Brookfield RVT, spindle C, Helipath) at 25° C.

TABLE 7

| INCI name | Trade Name/Supplier | % w/w |
|---|---|---|
| Phase A-1 | | |
| Water (demineralized) | | 75.00 |
| Glycerin | Glycerine 99%/Ruger | 3.00 |
| Phase A-2 | | |
| Xanthan gum | Vanzan NF/Vanderbilt | 0.20 |

TABLE 7-continued

| INCI name | Trade Name/Supplier | % w/w |
|---|---|---|
| Phase B | | |
| Caprylic/Capric Triglycerides | Myritol 318/BASF | 5.00 |
| Isoamyl Laurate | Dermofeel Sensolv/Evonik Dr. Straetmans GmbH | 2.50 |
| Ceeareth-20, Cetearyl Alcohol | Ritapro 200/Rita | 2.50 |
| Butyrospermum Parkii (Shea) Butter | Shea Butter Refined/Rita | 1.00 |
| Glyceryl Stearate SE | Cerasynt Q/Ashland | 1.50 |
| Cetyl Alcohol | Crodacol C-70/Croda | 1.00 |
| Stearic Acid | Stearic Acid/Rita | 1.50 |
| Isosorbide Dicaprylate | HydraSynol™ DOI/Sytheon | 2.50 |
| Phase C | | |
| Dipropylene Glycol Dibenzoate, Dipropylene Glycol | Dermoblend SYN/Alzo | 2.00 |
| Acetyl Zingerone | Synoxyl ® AZ/Sytheon | 0.50 |
| Phase D | | |
| Carbomer | Carpopol Ultez 10/Noveon | 0.30 |
| Sodium Hydroxide | Sodium Hydroxide Sol (10%) | 0.50 |
| Phase E | | |
| Ethylhexylglycerine, Caprylyl Glycol | Lexgard OE/Inolex | 1.00 |
| Total | | 100.00 |

Although the compositions and methods of the present specification as well as various commercial and consumer products containing/comprising the same have been described with respect to specific embodiments and examples, it should be appreciated that the present teachings are not limited thereto and other embodiments utilizing the concepts expressed herein are intended and contemplated without departing from the scope of the present teaching as intended in the true spirit and scope of the invention. It is therefore intended any and all modifications, variations, or equivalents that fall within the spirit and scope of the underlying principles are within the scope of this invention and are covered by the appended claims.

I claim:

1. A method of lightening skin and/or providing a more even tone to skin coloration said method comprising applying a skin lightening/even toning composition to those areas of the skin of an individual for which skin lightening/even toning is desired at least once a day until the skin coloration of the areas to which the composition was applied is more even and/or lighter than it was prior to application of the composition and/or has darkened less than those areas where the composition was not applied, said composition comprising (i) a skin lightening effective amount of aryl alkanone having the structure 1

Structure 1

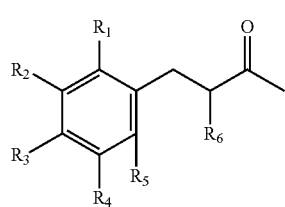

wherein $R_1$, $R_2$, $R_3$, $R_4$ and $R_5$ which may be the same or different, are independently H, OH, alkyl or alloy wherein the alkyl or alkoxy groups are linear or branched and have from 1 to 8 carbon atoms and $R_6$ is $COCH_3$ or $CO_2R_7$ wherein $R_7$ is a linear or branched alkyl having 1 to 8 carbon atoms and (ii) a dermatologically acceptable carrier.

2. The method of claim 1 where n the aryl alkanone is of the Structure 2

Structure 2

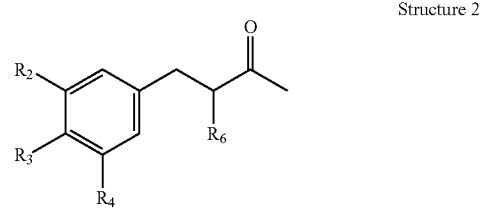

wherein $R_2$, $R_3$, and $R_4$, which may be the same or different, are independently OH or a linear alkoxy having, from 1 to 4 carbon atoms and $R_6$ is $COCH_3$ or $CO_2R_7$, wherein $R_7$ is a linear alkyl having 1 to 4 carbon atoms.

3. The method of claim 1 wherein the aryl alkanone is present in an amount of from 0.01 to 20 weight percent based on the total weight of the composition.

4. The method of claim 1 wherein the aryl alkanone is present in an amount of from about 0.05 to about 10 percent by weight based on the total weight of the composition.

5. The method of claim 1 wherein the aryl alkanone is acetyl zingerone.

6. The method of claim 1 wherein the skin lightening/even toning composition further comprises a second skin lightening agent in an amount of from about 0.01 to about 20 weight percent based on the total weight of the composition.

7. The method of claim 6 wherein the weight ratio of the aryl alkanone to the second skin lightening agent is from 20:1 to about 1:20.

8. The method of claim 1 wherein the aryl alkanone is present in an amount of from about 0.1 to about 5 wt % based on the total weight of the composition, a second skin lightening agent is present in an amount of from about 0.1 to about 5 wt % based on the total weight of the composition, and the weight ratio of the aryl alkanone to the second skin lightening agent is from about 10:1 to about 1:10.

9. The method of claim 6 wherein the second skin lightening agent is purified hexylresorcinol.

10. The method of claim 1 wherein the skin lightening/even toning composition further comprises one or more skin protective or treatment ingredients in an effective amount.

11. The method of claim 10 wherein the skin protective or treatment ingredients are selected from the group consisting of sunscreen actives, antioxidants, vitamins, anti-inflammatory agents, moisturizers, emollients, humectants, and mixtures thereof.

12. The method of claim 1 wherein the skin lightening/even toning composition is applied to all or essentially all areas of the skin to effect an overall skin lightening of the individual.

13. The method of claim 1 wherein the skin lightening/even toning composition is applied to those areas of the skin which have tanned due to exposure to sunlight and/or natural aging.

14. The method of claim 1 wherein the skin lightening/even toning composition is applied to those areas of the skin manifesting hyperpigmentation from other than sunlight or natural, aging.

15. The method of claim 1 wherein the skin lightening/even toning composition is applied to those areas of the skin manifesting post-inflammatory hyperpigmentation.

16. The method of claim 1 wherein the skin lightening/even toning composition is applied to those areas of the skin manifesting an uneven or blotched skin coloring.

17. The method of claim 1 wherein the skin lightening/even toning composition is applied to those areas of the skin manifesting skin darkening and/or uneven or blotched skin coloring resulting from diet, pregnancy, genetics, or drug therapy.

18. A method of mitigating the appearance of post-inflammatory hyperpigmentation and/or color unevenness or blotchiness in the skin of an individual, said method comprising applying a skin lightening/even toning composition comprising (i) an effective amount of an aryl alkanone having the Structure 1

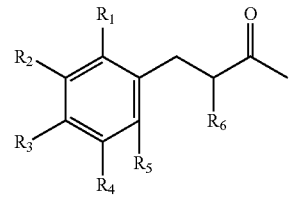

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms and $R_6$=$COCH_3$ or $CO_2R_7$, wherein $R_7$ is a linear or branched alkyl having 1 to 8 carbon atoms and (ii) a dermatologically acceptable carrier at least once a day to those areas of the skin which have suffered an inflammatory event, other than sunlight exposure, that leads to post-inflammatory hyperpigmentation and/or color unevenness or blotchiness, said event selected from a chemical exposure or drug/pharmaceutical treatment, laser and other light based therapy, acne, eczema, skin trauma or scarring, or insect bite or sting.

19. The method of claim 18 wherein the skin lightening/even toning composition is applied to areas of the skin that have suffered from acne, eczema, or an insect sting or bite or that have undergone laser therapy or chemical peel.

* * * * *